United States Patent [19]

Lerman

[11] Patent Number: 4,665,904
[45] Date of Patent: May 19, 1987

[54] CIRCULAR HINGE FOR ORTHOTIC BRACES

[76] Inventor: Max Lerman, 1950 Carla Ridge, Beverly Hills, Calif. 90210

[21] Appl. No.: 747,161

[22] Filed: Jun. 19, 1985

[51] Int. Cl.$^4$ ............................................. A61F 5/00
[52] U.S. Cl. .................................. 128/80 H; 16/221; 128/80 F; 403/163
[58] Field of Search ............... 128/80 H, 80 R, 80 C, 128/80 F, 80 D, 80 E, 80 S; 2/22; 16/221, 225, DIG. 13, 2; 403/163, 162, 161, 152

[56] References Cited

U.S. PATENT DOCUMENTS

| | | | |
|---|---|---|---|
| 3,742,517 | 7/1973 | Bednarczuk et al. | 2/22 |
| 3,898,697 | 8/1975 | Whitehead | 2/22 |
| 4,510,927 | 4/1985 | Peters | 128/80 H |
| 4,517,968 | 5/1985 | Greene et al. | 128/80 H |

Primary Examiner—Edgar S. Burr
Assistant Examiner—Moshe I. Cohen
Attorney, Agent, or Firm—Christie, Parker & Hale

[57] ABSTRACT

A preventive brace for supporting anatomical joints, such as the ankle joint, includes a semi-rigid leg-supporting shell conforming to the shape of the lower leg above the ankle joint, a semi-rigid foot-supporting shell conforming to the shape of the foot, and lateral and medial circular hinges rotatably securing the lateral and medial sides of the leg-supporting shell to the foot-supporting shell. The circular hinges are formed by relatively large area wall portions of the shells which overlie one another in the vicinity of the ankle bones (lateral and medial melleoli) projecting from the lateral and medial sides of the ankle. The overlying faces of the walls are rotatably interconnected along a circularly curved axis spaced outwardly from the ankle bone. In one embodiment, the circular hinge is centered generally on the ankle bone and traverses a circular path spaced a substantial distance outwardly from the ankle bone. The circular hinge allows the leg-supporting shell to rotate freely about the foot-supporting shell. A large open central region within each circular hinge prevents the supportive portions of the shell walls from applying pressure to the ankle bones. When the brace is secured to the ankle region, the large supportive walls of the shell provide substantial orthopedic support to the regions entirely around the lateral and medial melleoli. The circular hinge allows good freedom of movement of the brace while maintaining comfort by avoiding application of pressure to the ankle bones.

12 Claims, 8 Drawing Figures

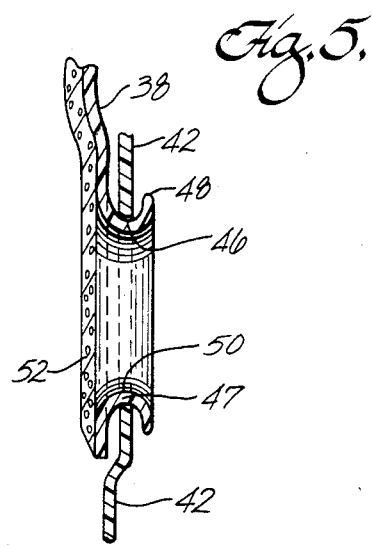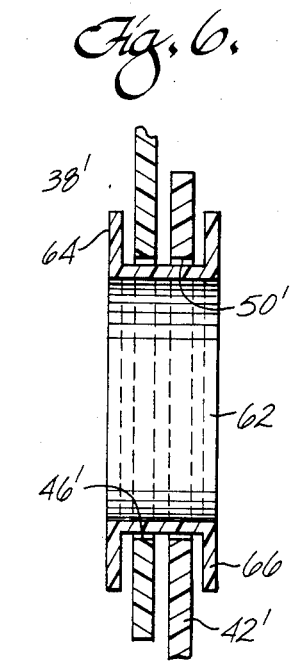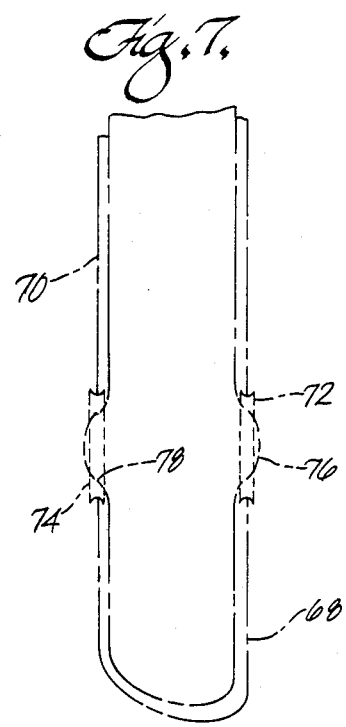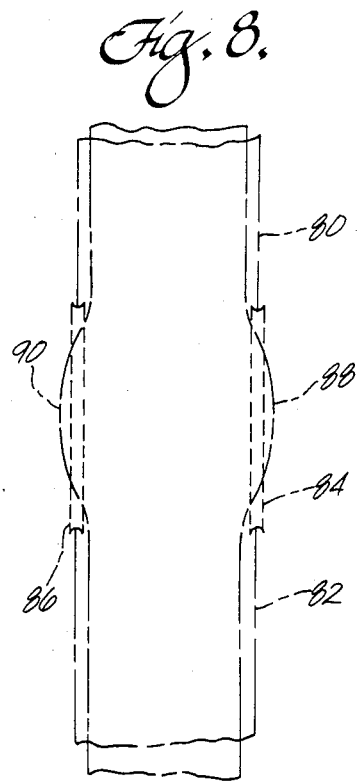

CIRCULAR HINGE FOR ORTHOTIC BRACES

FIELD OF THE INVENTION

This invention relates to orthotic braces, and more particularly to a circular hinge useful in combination with orthotic devices such as ankle braces and knee braces.

BACKGROUND OF THE INVENTION

Ankle sprains are injuries that commonly occur during sports activities. Sprained ankles are often wrapped with an ace bandage for immobilizing the ankle joint at least partially while the sprain heals. It normally takes a few weeks for an ankle sprain to heal. More severe ankle sprains are usually taped or placed in a cast.

In many sports injuries, an ankle sprain requires more support than can be provided by an ace bandage. For severe sprains not placed in a case, the trainer often tapes the ankle to provide additional support for protecting against stress placed on the ankle joint. In this way, a player can often continue playing or practicing on a sprained ankle. Taping an ankle to an extent that provides good support usually immobilizes the ankle joint to such an extent that it limits the athlete's performance level. The trainer also must be careful to protect against taping the ankle so tightly that circulation is cut off. Taping the ankle has the additional disadvantages of being costly and injurious to the skin.

There is a need for a lightweight and comfortable ankle brace that can be worn as a preventive brace during sports activities to prevent or at least reduce serious injuries to the ankle. Such ankle braces also are needed for preventing non-sports injuries or undue stress on the ankle joint for those persons who have weak joints possibly caused by arthritis or congenital defects, or for possibly less severe strains to the ligaments of the ankle. Such a preventive ankle brace should provide good lateral stability while maintaining freedom of ankle rotation. A common problem with present ankle braces is their inability to provide good lateral support without restricting ankle mobility and without creating discomfort during use. Ankle braces commonly include narrow upright support bars extending along the sides of the leg and hinged to a foot support by separate single axis joints. This ankle brace lacks good sideways stability. The upright bars also can press directly against the ankle bones and cause extreme discomfort if the brace is in close enough contact with the ankle joint to provide a reasonable amount of support.

The two bones which project from the ankle joint are known as the lateral and medial melleoli. Prior art ankle braces, worn in close contact with the lateral and medial melleoli in order to obtain sufficient support for the ankle joint, can be extremely uncomfortable. An undue amount of pressure is applied directly to the lateral and medial melleoli by the brace. For example, one prior art ankle brace that provides good lateral stability is a leather brace with a cut-out heel and laces in front, similar to a cast. The brace has rigid stays at its sides for lateral support. Although the cast-like brace provides a reasonable amount of lateral support for the ankle, the stays create pressure points on the ankle bones that can produce extreme discomfort. The cast also limits ankle mobility.

One embodiment of the present invention provides an ankle brace which is light in weight and does not significantly restrict freedom of normal ankle motion; and yet the brace provides good lateral stability for supporting the ankle joint while remaining unusually comfortable during use. The invention also provides braces for supporting other anatomical joints such as a knee brace or an elbow brace, for example.

SUMMARY OF THE INVENTION

Briefly, one embodiment of this invention provides a brace for supporting an anatomical joint about which a first anatomical member rotates relative to a second anatomical member. The brace includes first and second limb-supporting members having confronting faces overlying one another in the vicinity of the anatomical joint. A circular hinge rotatably interconnects the confronting faces of the limb-supporting members. The circular hinge permits the limb-supporting members to rotate relative to each other along a circularly curved arc spaced outwardly from the axis of the anatomical joint.

One embodiment of the invention is an ankle brace in which the first and second limb-supporting members comprise a semi-rigid leg-supporting shell and foot-supporting shell for conforming to the shape of the lower leg and the foot on opposite sides of the ankle joint. The circular hinge is formed by relatively large area wall portions of the shells which overlap one another in the vicinity of the ankle bones, i.e., the lateral and medial melleoli. The overlapping walls of the supporting shells are rotatably interconnected along a circularly curved arc shaped outwardly from the axis of the ankle bones. In one embodiment, the hinge rotates about the transverse axis through the ankle bones and traverses a circular path spaced a substantial distance outwardly from the ankle bones. The circular hinge allows the leg-supporting shell to pivot freely relative to the foot-supporting shell. A large central region within the circular hinge is left open, so that the supportive portions of the shell walls do not apply pressure to the ankle bones. When the brace is secured to the ankle region, the large area supportive walls of the shell produce substantial orthopedic support entirely around the lateral and medial sides of the ankle joint. The circular hinge also allows good freedom of movement while maintaining comfort by avoiding pressure on the ankle bones.

The ankle brace produces total contact with the ankle region entirely around each of the ankle bones. This produces good lateral support for the ankle joint. The two support members of the brace are also freely rotatable about the circular hinge, and therefore the brace does not restrict normal ankle rotation. The circular hinge passes around the ankle bones, and therefore avoids applying discomforting pressure to the ankle bones when the brace is wrapped with sufficient rigidity to offer good lateral support.

These and other aspects of the invention will be more fully understood by referring to the following detailed description and the accompanying drawings.

DRAWINGS

FIG. 5 is an enlarged semi-schematic cross-sectional view illustrating components of a circular hinge according to principles of this invention.

FIG. 6 is a fragmentary semi-schematic cross-sectional view illustrating an alternative embodiment of the circular hinge.

FIG. 7 is a schematic view illustrating an alternative use of the brace and circular hinge.

FIG. 8 is a schematic view illustrating a further alternative use of the brace and circular hinge.

DETAILED DESCRIPTION

Figure 1:
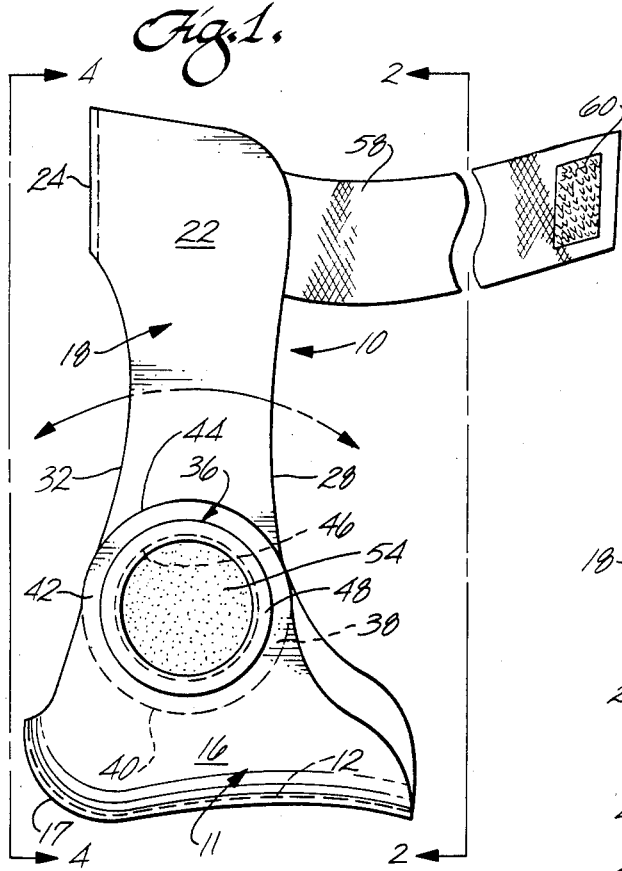
FIG. 1 is a fragmentary side elevation view showing an ankle brace according to principles of this invention.
Figure 2:
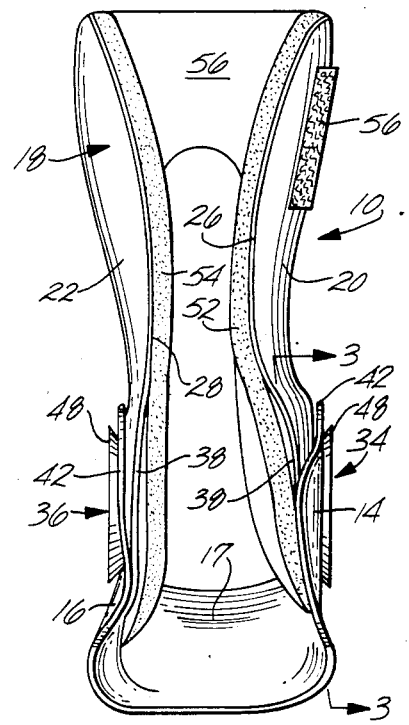
FIG. 2 is a front elevation view taken on line 2—2 of FIG. 1.
Figure 3:
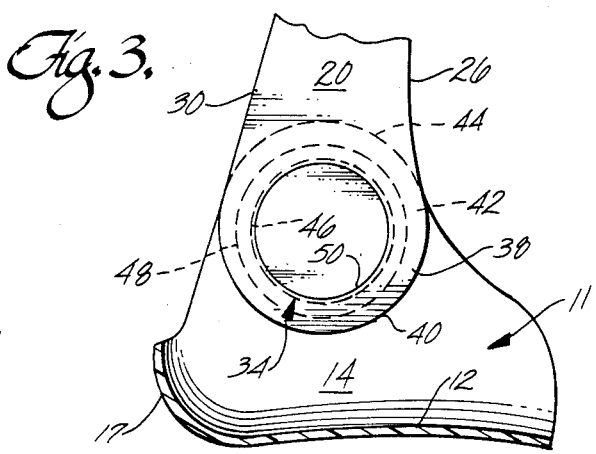
FIG. 3 is a fragmentary side elevation view taken on line 3—3 of FIG. 2.
Figure 4:
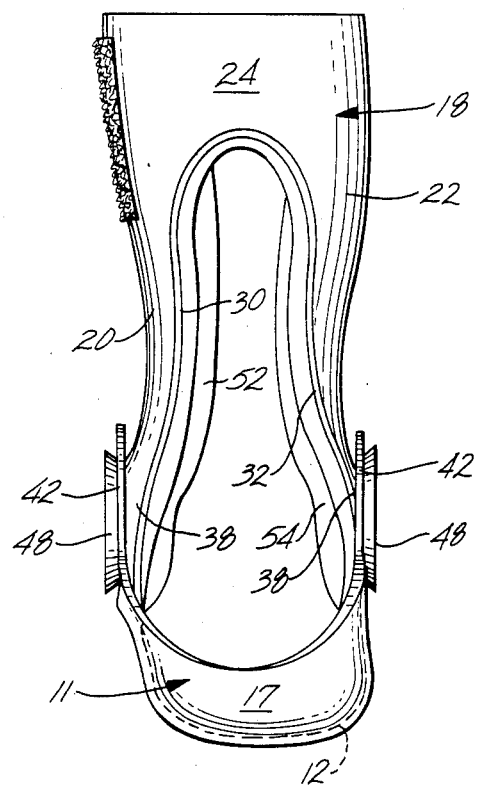
FIG. 4 is a rear elevation view taken on line 4—4 of FIG. 1.

FIGS. 1 through 5 illustrate an ankle brace 10 according to principles of this invention. The ankle brace includes a foot-supporting shell 11 having a bottom plate 12 for supporting the bottom of the foot. Upright lateral and medial sidewalls 14 and 16 extend around the lateral and medial sides of the foot plate. A rounded posterior wall 17 extends around the heel. The shell is preferably made from a semi-rigid, thin wall, plastic material, such as polyethylene. The shell conforms closely to the shape of the foot and can be worn inside the user's shoe, if desired.

The ankle brace also includes a leg-supporting shell 18 for supporting the lower leg above the ankle joint. The leg-supporting shell includes elongated lateral and medial uprights 20 and 22 for extending along lateral and medial sides of the lower leg above the ankle joint. A rounded rear wall 24 is formed integrally with upper portions of the uprights for extending around the calf region of the lower leg. The leg-supporting shell is made from a semi-rigid, thin wall plastic material, such as polyethylene. The leg-supporting shell conforms closely to the shape of the lower leg above the ankle region. The lateral and medial uprights are curved in cross section to conform to the shape of the lateral and medial sides of the legs above the ankle joint. The rear wall 24 conforms to the shape of the calf region. A long, narrow open space is left between upright front edges 26 and 28 of the lateral and medial uprights. The lateral and medial uprights also have spaced apart upright rear edges 30 and 32 extending along a narrow opening left between the rear portions of the uprights. Thus, the uprights are freely bendable inwardly or outwardly along most of their length so as to independently conform to the shape of the lower leg when wrapped tightly into contact with the lower leg during use.

The leg-supporting shell 18 is rotatably attached to the foot-supporting shell 11 through lateral and medial circular hinges 34 and 36, respectively. The circular hinges are identical in construction. They allow the leg-supporting shell 18 to rotate as a unit about a transverse axis through the sides of the foot-supporting shell 11. Axes of rotation of the two circular hinges are aligned on a transverse common axis through the user's ankle joint, when the brace is worn.

Inasmuch as the two circular hinges are identical, only one of the circular hinges will now be described. The lower portion of each upright 20, 22 is relatively wide so that a lower face 38 of each upright overlies a substantial area surrounding the ankle bone during use. The lower face 38 of each upright is generally flat and is on the inside of the circular hinge. The lower face of each upright terminates in a circularly curved, U-shaped bottom edge 40.

The upper portion 42 of each sidewall 14, 16 of the foot-supporting shell 11 overlies the outside surface of a corresponding lower face 38 of the upright. The upper portion 42 of each sidewall of the foot support is relatively wide so it overlies a substantial area of the lower face 38 of the adjacent upright. The upper portion 42 of each sidewall of the foot support thus forms a generally flat outside face of the circular hinge. The upper portion 42 of each sidewall terminates in a circularly curved, inverted U-shaped upper edge 44.

A large circular hole 46 extends through the upper portion 42 of each sidewall of the foot support. The lower face 38 of each upright has a tubular extension 47 with a circular flanged outer lip 48 surrounding a large circular hole 50 extending through the tubular extension 47 aligned with the large hole 46 in the sidewall of the foot support. The circular hole 50 in the lower face of the upright is slightly shorter in diameter than the diameter of the hole 46. In one embodiment, the diameter of the hole 50 is about 2¼ inches. The width of the circular hinge is about 3½ inches. As shown best in FIG. 5, the circular flanged lip 48 on each upright extends over the edge of the circular hole 46 in the adjacent wall of the foot support. The lip is then bent back with a reverse bend so it rotatably interconnects with the edge of the hole 46 around the entire circumference of the hole. The reverse bend formed in the circular flanged lip extends back far enough so that the lip overlaps the outer face of the sidewall 42 of the foot support. This rotatably secures the foot support to the bottom of the lateral and medial uprights 20 and 22, allowing free relative rotation between the foot support and the leg support about a transverse axis through the center of the aligned holes 50 on opposite sides of the brace. The rotatable connection between each tubular extension 47 and its flanged lip and the openings 46 in the uprights thus prevents longitudinal motion of the foot support relative to the leg support, i.e., it limits relative motion of these two components toward each other or away from each other along a longitudinal axis through the leg support to the foot support.

The view illustrated in FIG. 5 is exaggerated to clearly show the spacing between the components of the circular hinge. There is a slight amount of slack left between the edge of the circular hole 46 in each upright and the base of the annular groove formed between the sidewall of the foot support and the inside of the flanged lip. This allows the foot support to move longitudinally a short distance (about 1/16 inch) relative to the length of the upright. The base of the annular groove formed by the flanged lip also is slightly wider than the thickness of the sidewall of the foot support. This allows a short amount (less than 1/16 inch) of sideways travel between the sidewalls of the foot support and the uprights of the leg support. The combined slack between the component parts of the circular hinge permits a slight rocking motion of the foot support relative to the leg support. Moreover, the walls of the leg and foot supports are bendable somewhat to assist in the rocking motion during use. Thus, the brace is able to accommodate the natural sideways rocking motion of the foot relative to the lower leg.

In one embodiment, the leg support and foot support are each made of ⅛ inch thick high density polyethylene. Both components are heat formed in the desired shape. The regions around the openings 46 in the lower portions of the uprights are heated, bent over and hammered to fit the uprights to the foot plate and form the flanged lip of the circular hinge. High density polyethylene is an exceedingly low friction material which enhances the function of the ankle brace. The confronting faces 38 and 42 are somewhat slippery, which assists in freely rotating the foot-supporting shell relative to the leg-supporting shell.

The ankle brace also includes interior padding in the form of a resilient plastic foam piece having upright lateral and medial sections 52 and 54 and a rear portion 56 at the top rear of the leg support. The lower portions of the upright foam sections 52 and 54 cover the inside faces of the uprights 20 and 22, including the insides of the openings 50 through the circular hinges. The foam padding is preferably a heat formed, closed cell polyester foam material commonly used as compressible padding for orthopedic supports.

The braces can be secured to the ankle region by a variety of strap-type fasteners. In the illustrated embodiment, a section 56 of a Velcro-type pile material is adhesively bonded to an upper outer face of the lateral upright 20. An elongated, flexible, elastically stretchable fastening strap 58 is releasably secured to the fastener section 56. In one embodiment, the strap 58 can comprise a composite material having a length of neoprene rubber with layers of soft, flexible elastic fabric materials on its opposite faces. The outside face of the neoprene rubber strap 58 can have a roughened pile-type surface that releasably attaches and adheres to a Velcro-type hook material. The inside face of the strap 58 has sections 60 of a Velcro hook material secured to it by stitching. One of the Velcro hook sections 60 (not shown) releasably attaches the strap to the fastener section 56 at the top of the leg-supporting shell. The strap is then wrapped around the lower leg and around the upper portion of the leg-supporting shell. The hook fastener 60 at the free end of the strap is then releasably adhered to the outer surface of the strap 58 to hold the tension applied to the upper portion of the leg-supporting shell by the elastically stretchable strap 58.

In using the ankle brace, the user's foot is placed within the foot-supporting shell. The sidewalls of the foot support extend over the lateral and medial sides of the foot and are bent to conform to the shape of the foot. The uprights of the leg-supporting shell are spread apart and fitted around the sides of the user's lower leg above the ankle joint. The uprights of the leg support are bendable to conform to the shape of the lower leg. The confronting inside and outer faces 38 and 42 of the circular hinge overlie a substantial surface area at the lateral and medial sides of the ankle joint. These portions of the circular hinge provide total contact with the sides of the ankle entirely around each ankle bone. The openings 50 within the circular hinges are centered on the ankle bones so that the outwardly projecting portions of the ankle bones are positioned inside the openings in the circular hinges. The strap 58 is then tightened around the top of the brace to tightly secure the ankle brace around the ankle.

The large area confronting faces 38 and 42 of the brace hug the sides of the ankle entirely around each ankle bone to provide good lateral support for the ankle. The ankle brace does not immobilize the ankle joint or otherwise restrict its normal rotational motion. The foot-supporting shell and leg-supporting shell are freely rotatable relative to one another about the transverse axis through the circular hinge. There is also enough slack in the ankle brace that the foot-supporting shell can be rocked from side to side slightly relative to the leg-supporting shell. The brace is also comfortable and light in weight, and therefore it is particularly useful as a preventive brace, especially one that can be used in sports activities. The openings in the circular hinges are sufficiently large that the supportive portions of the brace are spaced a substantial distance outwardly from the projecting ankle bones. Thus, only the resilient foam padding in the interior of the brace is in direct contact with the ankle bones.

The ankle brace also provides added strength to the region around the ankle joint, thereby enhancing stability of the brace for its support to the ankle region. The overlapping circular faces of the leg-supporting shell and the foot-supporting shell add strength to the portion of the brace which is in direct contact with the region around each ankle bone. In addition, the flanged lip of the hinge is bent to overlap the other portions of the circular hinge; and these portions of the hinge also provide additional sideways strength to the brace.

FIG. 5 illustrates one embodiment of the circular hinge. In an alternative embodiment (not shown), the circular hinge portions of the leg-supporting shell and foot-supporting shell can be reversed so that the upper sidewall portion 42 of the foot-supporting shell is on the inside of the hinge and the lower face 38 of the leg-supporting shell is on the outside of the circular hinge.

FIG. 6 shows a further alternative embodiment in which a cylindrical ring 62 forms the circular hinge. In this embodiment, the lower face 38' of the leg-supporting shell overlies an adjacent face 42' at the upper portion of the foot-supporting shell. The lower face 38 has a circular opening 46' with essentially the same diameter as a circular opening 50 in the upper face 42' of the foot-supporting shell. The cylindrical hinge 62 is inserted through these two openings. The hinge includes inner and outer annular flanges 64 and 66 adjacent the faces 38' and 42' of the leg support and foot support. The cylindrical ring 62 thus rotatably interconnects the foot-supporting shell with the lower leg-supporting shell. Use of the embodiment shown in FIG. 6 is similar to that of the brace shown in FIGS. 1 through 5. The projecting ankle bones are aligned with the opening in the circular hinge so that the brace, when attached to the user's ankle, does not apply pressure to the ankle bones, owing to the large opening within the circular hinge.

FIG. 7 is a schematic illustration of an alternative use of the brace and circular hinge. In this embodiment, the brace is an ankle brace and is attached to a shoe 68. A lower leg-supporting shell 70 is similar to the leg-supporting shell 18 described above. The leg-supporting shell 70 is attached to portions of the shoe 68 which interconnect with the circular hinge in a manner similar to that shown in FIGS. 1 through 5 or in the embodiment of FIG. 6. In FIG. 7, the lateral and medial circular hinges 72 and 74 are schematically illustrated and are shown with the lateral and medial ankle bones 76 and 78 projecting through openings in the circular hinges.

FIG. 8 shows a further alternative use of circular hinge in a knee brace. In this embodiment, an upper leg-supporting shell 80 is attached to the upper leg above the knee joint, and a lower leg-supporting shell 82 is attached to the lower leg below the knee joint. The upper and lower shells are interconnected through circular hinges 84 and 86 in a manner similar to that described above. FIG. 8 schematically illustrates projecting lateral and medial portions 88 and 90 of the knee joint centered within the openings of the circular hinges 84 and 86. The knee brace of FIG. 8 provides good support around the lateral and medial sides of the knee joint and permits free relative rotation of the upper and lower legs, while avoiding pressure points applied to the bony protuberances at opposite sides of the knee joint.

The circular hinge of the invention also can be used in other similar braces such as an elbow brace or a wrist brace.

I claim:

1. A brace for supporting an anatomical joint about which a first anatomical member rotates relative to a second anatomical member, the anatomical joint having an outwardly projecting bone on the lateral or medial side of the joint, the brace comprising:

a first support member for orthopedically supporting the first anatomical member adjacent the anatomical joint;

a second support member for orthopedically supporting the second anatomical member on an opposite side of the anatomical joint;

the first and second support members having confronting faces overlying one another adjacent the joint;

a large substantially circular first opening in the confronting face of the first member; and circular hinge means having a tubular extension affixed to the confronting face of the second support member and extending laterally through the first opening in the first support member, the tubular extension having a large second opening through it aligned with the first opening, the tubular extension having an annular outer lip overlapping an outer face of the first support member around said first opening for rotatably interconnecting the confronting faces of the first and second support members for causing free relative rotation of the support members about a transverse axis through the first and second openings while joining the support members in a side-by-side relation substantially limiting relative lateral motion and relative longitudinal motion of the support members;

the first and second openings being sufficiently large to allow the bone projecting from the side of the anatomical joint to project into said openings to avoid pressure contact between the projecting portion of the bone and the orthopedically supportive interconnected faces of the first and second support members when the brace is worn so that said support members provide orthopedic support for the anatomical joint.

2. Apparatus according to claim 1 in which the brace comprises an ankle brace; and in which the first support member is a foot support, the second support member is a leg support, and the openings in the circular hinge means encircle the melleolus bone of the ankle.

3. Apparatus according to claim 1 including a layer of resilient padding on an inside face of the support member closest to the anatomical joint and overlying the first and second openings.

4. Apparatus according to claim 1 in which the brace cmprises a pair of said circular hinge means rotatably interconnecting lateral and medial sides of the first and second support members, so the axes of rotation of the circular hinge means are aligned with one another and so that portions of the bones on the lateral and medial sides of the anatomical joint project into the large first and second openings in the circular hinge means on the lateral and medial sides of the joint.

5. A brace for supporting an anatomical joint about which a first anatomical member rotates relative to a second anatomical member, the anatomical joint having an outwardly projecting bone adjacent one side of the joint, the brace comprising:

a first limb-supporting member for orthopedically supporting the first anatomical member;

a second limb-supporting member for orthopedically supporting the second anatomical member;

the first and second limb-supporting members having confronting faces overlying one another adjacent the joint;

a large substantially circular first opening in the confronting face of the first limb-supporting member; and circular hinge means joined to the confronting face of the second limb-supporting member and having an annular outer lip overlapping the outer face of the first limb-supporting member to rotatably interconnect the confronting faces of the first and second members to allow free relative rotation of the members about a transverse axis through the first and second openings while joining the first and second members in a side-by-side relation to substantially prevent relative lateral motion and relative longitudinal motion of the two members, the first and second openings being sufficiently large to allow the bone adjacent the side of the anatomical joint to project into the openings so that when the first and second limb-supporting members are secured to the first and second anatomical members to provide orthopedic support for the anatomical joint, the bone projects into said openings to avoid pressure contact on the bone from the orthopedically supportive interconnected faces of the first and second limb-supporting members.

6. Apparatus according to claim 5 in which the brace comprises an ankle brace; and in which the first support member is a foot support, the second support member is a leg support, and the openings in the circular hinge means encircle the melleolus bone of the ankle.

7. Apparatus according to claim 5 including a layer of resilient padding on an inside face of the first support member and overlying the openings in the first and second support members.

8. Apparatus according to claim 5 in which the brace comprises a pair of said circular hinge means rotatably interconnecting lateral and medial sides of the first and second members so the axes of rotation of the circular hinge means are aligned with one another and so that portions of the bones on the lateral and medial sides of the anatomical joint project into the large openings of the circular hinge means on the lateral and medial sides of the joint, respectively.

9. Apparatus according to claim 5 in which the hinge means join the limb-supporting members along a circular arc formed in a sidewall of the first support member rotatably interlocking with a narrow annular groove formed by the tubular extension carried on the second limb-supporting member.

10. Apparatus according to claim 9 in which the tubular extension comprises a thin wall of the second limb-supporting member integrally formed with the second limb-supporting member and extending as a tubular member through the first opening in the first limb-supporting member for forming said annular groove, said annular lip on the tubular extension of the second limb-supporting member rotatably interlocking the first limb-supporting member in said annular groove.

11. An ankle brace for supporting the ankle joint, wherein the lateral and medial melleoli bones project outwardly from lateral and medial sides of the ankle joint, respectively, the brace comprising:
- a leg-supporting member for supporting the lower leg above the ankle joint;
- a foot-supporting member for supporting the foot below the ankle joint;
- the leg- and foot-supporting members having corresponding pairs of confronting faces overlying one another adjacent the ankle joint on the lateral side and on the medial side of the ankle joint;
- large substantially circular first lateral opening in a first of said confronting faces adjacent the lateral side of the ankle joint;
- a large substantially circular first medial opening in a first of said confronting faces on the medial side of the ankle joint; and
- lateral and medial circular hinge means for rotatably interconnecting the confronting faces of the leg- and foot-supporting members for relative rotation about a common transverse axis through the ankle joint, each circular hinge means having a corresponding tubular extension affixed to a second of said confronting faces and extending through the first opening in the adjacent first confronting face, each tubular extension having a large second opening through it aligned with the adjacent first opening, each tubular extension having a corresponding outer lip overlapping the adjacent first confronting face for rotatably interconnecting the confronting faces of the leg- and foot-supporting members on the lateral and medial sides of the brace,
- the first and second openings in the hinge means on the lateral and medial sides of the brace being aligned to rotate about said transverse axis through the ankle joint, the first and second openings in the circular hinge means on the lateral and medial sides of the ankle brace also being sufficiently large to allow the lateral and medial melleoli bones to project into the first and second openings on the lateral and medial sides of the brace, respectively, so that when the leg- and foot-supporting members are secured to the leg and foot to provide orthopedic support for the ankle joint, the interconnected orthopedically supportive confronting faces of the leg- and foot-supporting members substantially avoid applying pressure to the lateral and medial melleoli bones of the ankle joint.

12. Apparatus according to claim 11 in which the leg- and foot-supporting members are joined along a corresponding circular arc formed by a sidewall of the first of the confronting face rotatably interlocking with a narrow annular groove formed by the tubular extension on the second confronting face.

* * * * *

UNITED STATES PATENT AND TRADEMARK OFFICE
CERTIFICATE OF CORRECTION

PATENT NO. : 4,665,904

DATED : May 19, 1987

INVENTOR(S) : Max Lerman

It is certified that error appears in the above-identified patent and that said Letters Patent is hereby corrected as shown below:

In the Abstract:
Line 11, change "melleoli" to --malleoli--; line 25, change "melleoli" to --malleoli--.

In the Specification:
Column 1, line 19, change "case" to --cast--, lines 52, 54 and 57, change "melleoli" to --malleoli--. Column 2, line 28, change "melleoli" to --malleoli--; line 31, delete "shaped" and insert therefor --spaced--; lines 63, 66 and 67, change "line" to --lines-- (all occurrences). Column 4, line 12, delete "extending" and insert therefor --extends--. Column 5, line 1, change "assists" to --assist--.

In the Claims:
Column 7, line 53, change "melleolus" to --malleolus--; line 59, change "cmprises" to --comprises--. Column 8, line 39, change "melleolus" to --malleolus--. Column 9, line 2, change "melleoli" to --malleoli--. Column 10, lines 12 and 21, change "melleoli" to --malleoli--.

Signed and Sealed this

Nineteenth Day of July, 1988

Attest:

DONALD J. QUIGG

Attesting Officer

Commissioner of Patents and Trademarks